US008237844B2

(12) United States Patent
Blais-Ouellette et al.

(10) Patent No.: US 8,237,844 B2
(45) Date of Patent: Aug. 7, 2012

(54) SPECTROGRAPHIC MULTI-BAND CAMERA

(75) Inventors: Sebastien Blais-Ouellette, Laval (CA); Ed Wishnow, Berkeley, CA (US)

(73) Assignee: Photon etc. inc., Montreal (CA)

( * ) Notice: Subject to any disclaimer, the term of this patent is extended or adjusted under 35 U.S.C. 154(b) by 1320 days.

(21) Appl. No.: 11/912,663

(22) PCT Filed: Apr. 25, 2006

(86) PCT No.: PCT/CA2006/000665
§ 371 (c)(1),
(2), (4) Date: Oct. 25, 2007

(87) PCT Pub. No.: WO2006/113996
PCT Pub. Date: Nov. 2, 2006

(65) Prior Publication Data
US 2008/0252731 A1    Oct. 16, 2008

Related U.S. Application Data

(60) Provisional application No. 60/674,685, filed on Apr. 26, 2005.

(51) Int. Cl.
H04N 5/225       (2006.01)
H04N 5/335       (2011.01)
(52) U.S. Cl. .................... 348/342; 348/143; 348/162
(58) Field of Classification Search ............... 348/162, 348/143, 342, 33
See application file for complete search history.

(56) References Cited

U.S. PATENT DOCUMENTS

| 5,132,802 | A | 7/1992 | Osthues et al. |
| 5,867,264 | A | 2/1999 | Hinnrichs |
| 6,236,881 | B1 | 5/2001 | Zahler et al. |
| 6,353,673 | B1 | 3/2002 | Shnitser et al. |
| 6,849,844 | B2 | 2/2005 | Khoury |
| 7,238,940 | B1 * | 7/2007 | Davidson et al. ............ 250/330 |
| 2005/0195484 | A1 | 9/2005 | Blais-Ouellette |

OTHER PUBLICATIONS

Bardens, Samuel C.; Arns, James A.; Colburn, Willis S.; and Williams Joel B. "Volume-Phase Holographic Gratings and the Efficiency of Three Simple Volume-Phase Holographic Gratings" Pub. of the Astronomical Soc. of the Pacific, 112;809-820, Jun. 2000.

* cited by examiner

Primary Examiner — David Lazaro

(57) ABSTRACT

The present invention concerns a method and camera for obtaining a high-contrast image of a predetermined target present in an area under observation. The method involves obtaining an in-band image of the observation area including the target using a filter whose bands are aligned with selected characteristic wavelength bands of the target and an out-of-band image of the observation area excluding the target using the filter with its bands non-aligned with the selected characteristic wavelength bands of the target. Processing of the in-band and out-of-band images results in a high-contrast image highlighting the presence of the target in the observation area and thereby allowing its detection and monitoring.

22 Claims, 4 Drawing Sheets

A)   C)

B)   D)   E)

IN-BAND IMAGE      OUT-OF-BAND IMAGE      HIGH-CONTRAST IMAGE

SPECTROGRAPHIC MULTI-BAND CAMERA

FIELD OF THE INVENTION

The present invention relates to the field of 2D imaging and more particularly concerns a spectrographic multi-band camera which can be used for the detection and monitoring of predetermined types of molecules.

BACKGROUND OF THE INVENTION

Spectrography is a well known technique for determining the presence of a given molecule in an area under observation. As each molecule has predetermined absorption and emission spectra, correlating the known positions of its absorption or transmission lines with the obtained spectrogram allows for its detection and tracking in a non-interfering manner. Imaging the area under observation at many wavelengths, including at the wavelength of these absorption or transmission lines, is one way to do imaging spectrography. Devices used for these purposes generally involve a scanning technique based on a Fabry-Perot etalon or Fourier Transform Spectrograph, where each target absorption or transmission band is imaged individually and sequentially. This approach however makes the process inefficient and good signal to noise ratios are difficult to obtain.

There is therefore a need for a more practical camera and imaging technique for molecule detection and monitoring.

SUMMARY OF THE INVENTION

Accordingly, the present invention provides a method for obtaining a high-contrast image of an observation area, the observation area including at least one contrast target, where light from the contrast target has a spectral profile characterised by a plurality of predetermined spectral bands. The method includes the steps of:
 a) providing a camera including an optical filter having spectral filtering characteristics matching the plurality of predetermined spectral bands;
 b) obtaining an in-band filtered image of said observation area using said camera, said obtaining an in-band filtered image comprising the substeps of:
  i. receiving a first multi-band light signal from said observation area; and
  ii. filtering said first multi-band light signal, said filtering said first multi-band light signal comprising impinging said first multi-band light signal on said filter from an angle selected to provide an alignment of the spectral filtering characteristics of the filter with the plurality of predetermined spectral bands of the contrast target;
 c) obtaining an out-of-band filtered image of said observation area using said camera, said obtaining an out-of-band filtered image comprising the substeps of:
  i. receiving a second multi-band light signal from said observation area; and
  ii. filtering said second multi-band light signal, said filtering said second multi-band light signal comprising impinging said second multi-band light signal on said filter from an angle selected to provide a non-alignment of the spectral filtering characteristics of the filter with the plurality of predetermined spectral bands of the contrast target; and
 d) subtracting one of said in-band filtered image and out-of-band filtered image from the other to obtain said high-contrast image of the observation area.

In another aspect, the present invention provides a camera for obtaining a high-contrast image of an observation area, the observation area including at least one contrast target, light from the contrast target having a spectral profile characterised by a plurality of predetermined spectral bands. The camera includes an optical filter having spectral filtering characteristics matching the plurality of predetermined spectral band and an imaging device for imaging light outputted by the optical filter. It also includes an optical arrangement for directing light from the observation area onto the optical filter at an impinging angle, the optical arrangement having an in-band mode for obtaining an in-band filtered image of the observation area at the imaging device, and an out-of-band mode for obtaining an out-of-band filtered image of the observation area at the imaging device, wherein in the in-band mode the impinging angle is selected to provide an alignment of the spectral filtering characteristics of the filter with the plurality of predetermined spectral bands of the contrast target, and wherein in the out-of-band mode the impinging angle is selected to provide a non-alignment of the spectral filtering characteristics of the filter with the plurality of predetermined spectral bands of the contrast target. It further includes processing means for processing the in-band and out-of-band images, the processing comprising subtracting one of the in-band filtered image and out-of-band filtered image from the other to obtain the high-contrast image of the observation area.

Preferably, the optical filter includes a Volume Bragg Grating.

Advantageously, the optical filter may be used in either bandpass or bandstop mode to obtain the in-band and out-of-band images. The optical filter may be of a transmission type or reflection type.

In use, the camera takes an in-band image of the observation area with the predetermined spectral bands of the contrast target (for example, of the molecule) under observation in alignment with the spectral filtering characteristics of the filter. The camera then takes an out-of-band image of the observation area with the spectral bands of the contrast target under observation out of alignment, i.e. in non-alignment, with the spectral filtering characteristics of the filter. The resulting in-band and out of-band images are subtracted to obtain a high-contrast image, which highlights the zones where the contrast target is present. In this manner, specific molecules may be detected and monitored in real time.

Other features and advantages of the present invention will be better understood upon reading of preferred embodiments thereof with reference to the enclosed drawings.

BRIEF DESCRIPTION OF THE DRAWINGS

FIG. 3A shows the in-band filtered spectrum of the observation target, and FIG. 3B shows the corresponding in-band filtered image.

DESCRIPTION OF PREFERRED EMBODIMENTS OF THE INVENTION

The present invention relates to the field of 2D imaging for the detection and monitoring of selected targets. A description of preferred embodiments of the invention with reference to FIGS. 1 to 5 follows.

Method for Obtaining a High-Contrast Image

In accordance with one aspect of the present invention, there is provided a method for obtaining a high-contrast image of an observation area, more precisely of specific selected targets which may be present in the area.

There is an ever increasing need for on-line real-time detection and monitoring in such diverse fields as biomedicine and the pulp and paper industry. The "target" referred to in the present description may therefore be embodied by any molecule, combination of molecules, or entity having a predetermined spectral profile, and may be in gaseous, liquid or solid form. The "observation area" may in turn be embodied by any surrounding media in which the target may find itself. For simplicity, the light originating from any element within the observation area other than the target will be referred herein as the "background". It will be clearly understood however, that this expression is not meant to designate the relative position of the different elements in the observation area with respect to each other.

Detection and monitoring of various molecules in the human body is useful in the study and prevention of diseases. As such, the observation area may be a biological site, for example the retina in the human body, and the target may be a specific type of molecule, for example glucose. In another application, the observation area may be an environmental or industrial sample, such as wood or pulp in paper mills, and the target may be water molecules so as to determine the moisture content of the wood sample. In yet another application, the observation area may be a product in a fabrication plant, for example a powder or pharmaceutical tablet, and the target may be a particular molecule of a residual synthesis by-product.

Figure 1:
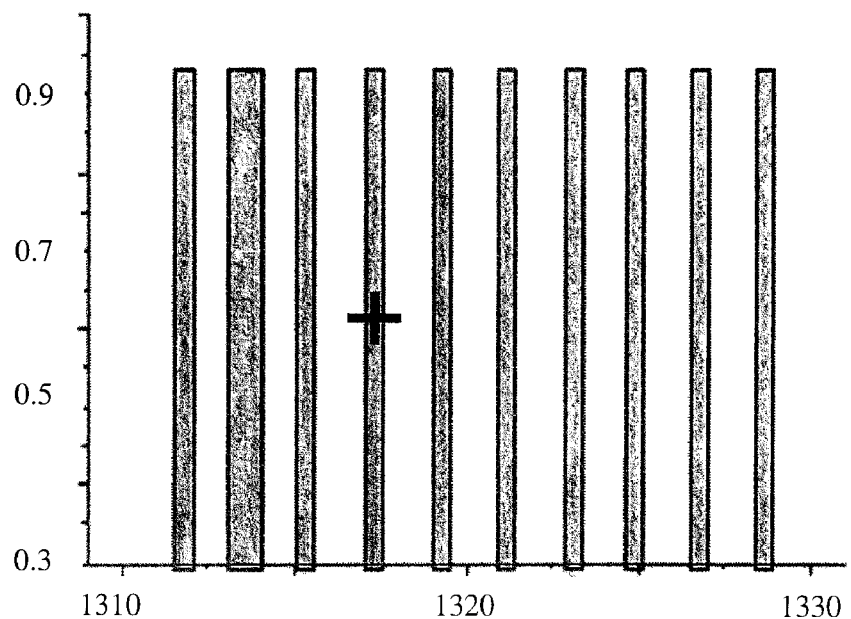
FIG. 1 is a graph showing the spectral filtering characteristics of a typical filter of a camera according to a preferred embodiment of the invention.
Figure 2:
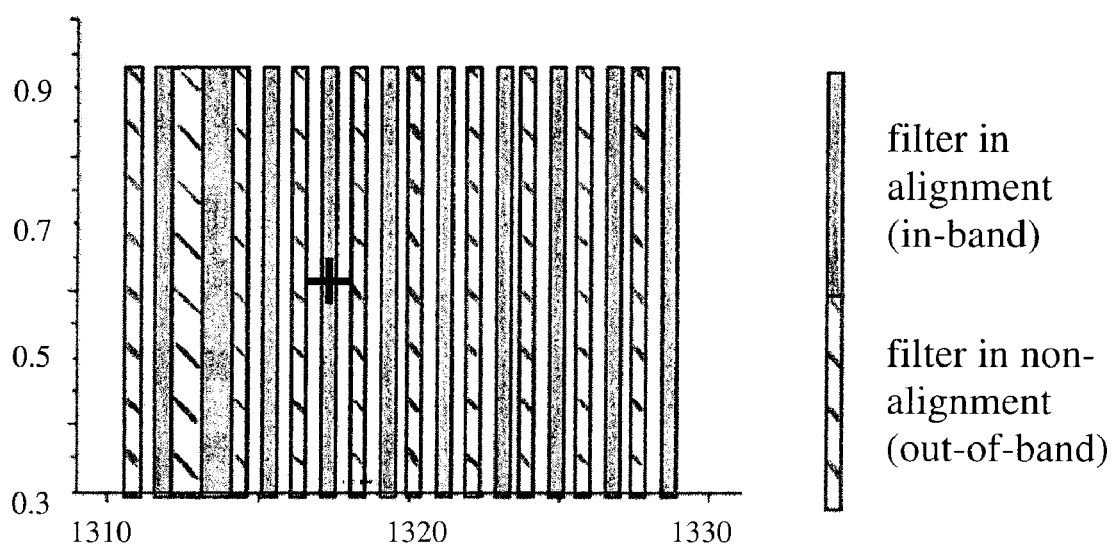
FIG. 2 is a graph illustrating the spectral filtering characteristics of the filter when the filter is in alignment (in-band) and in non-alignment (out-of-band) with the predetermined bands of the spectral profile of the target shown in FIG. 1.
Figure 3:
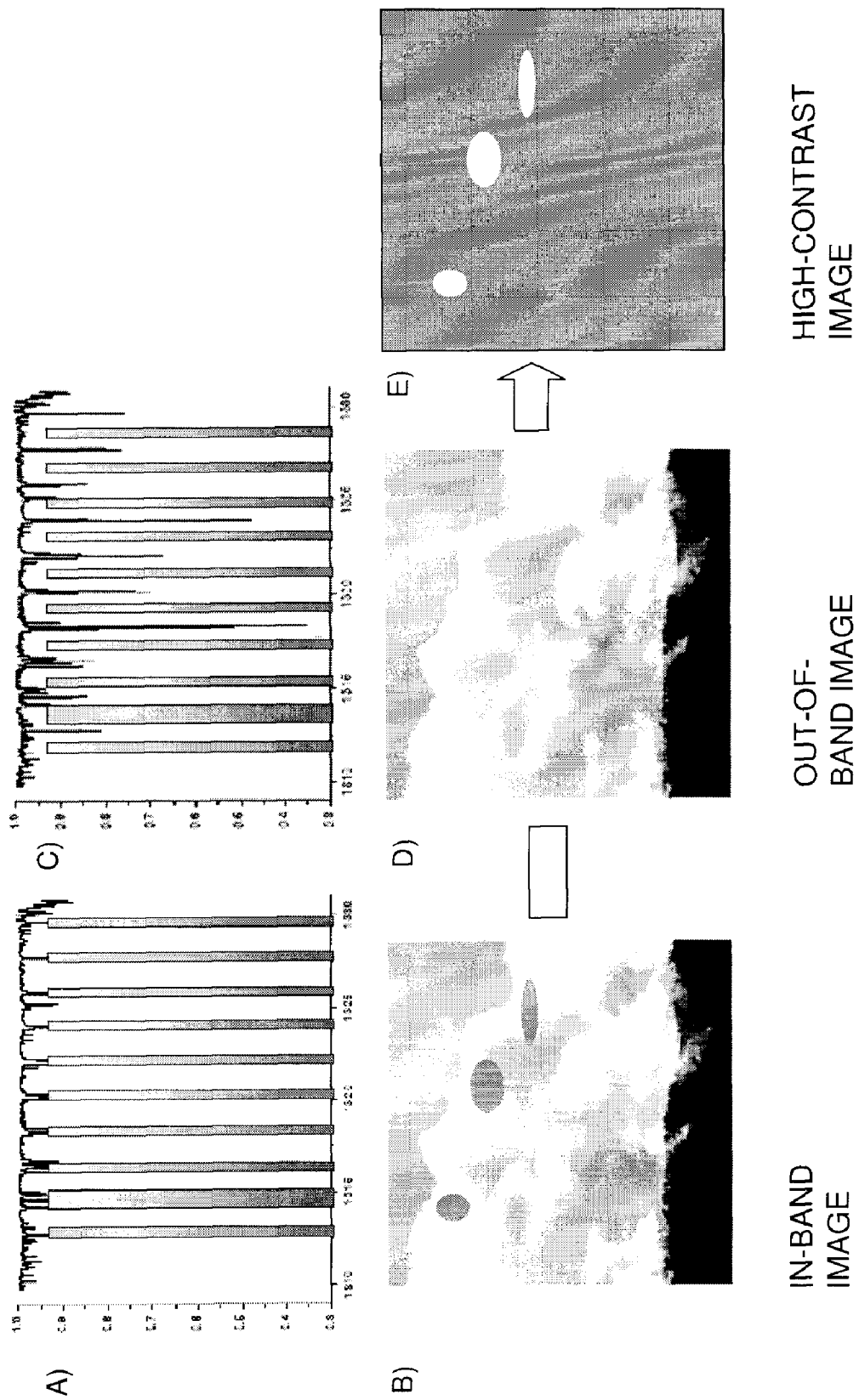
FIGS. 3A to 3B illustrate the generation of a high-contrast image from initial in-band and out-of-band images.
FIG. 3C shows the out-of-band filtered spectrum of the observation target.
FIG. 3D shows the corresponding out-of-band filtered image.
FIG. 3E shows the high contrast image obtained from the subtraction of the in-band image of FIG. 3B from the out-of-band image of FIG. 3D

Multi-band light from the target has a specific spectral profile characterized by either emission or absorption spectral bands, as shown in FIG. 1. The present invention may use either the emission or absorption bands of a given target, which are both referred to as "spectral bands". The spectral bands of a target are predetermined, that is, are known characteristics intrinsic to the target.

The background of the observation area is assumed to emit light at wavelengths across the spectrum of interest, including at wavelengths corresponding to the characteristic spectral bands of the target.

Detection and monitoring of a target is carried out by obtaining a high-contrast 2D image of that target within the observation area. The method of obtaining such a high-contrast image generally involves the steps of:

a) providing a camera which includes an optical filter having spectral filtering characteristics matching the spectral bands of that target;

Different embodiments of such a camera are shown further below. The filter is preferably a volume Bragg grating, which can be manufactured with reflection or transmission filter bands distributed according to a desired spectral profile, as is well known to one skilled in the art. Owing to filter cost and material, it may be preferable to consider only those bands in the range from 300 nm to 2500 nm.

b) obtaining an in-band filtered image of the observation area using the camera;

Using the camera provided, an in-band filtered image is obtained, as depicted in FIGS. 3A and 3B. In the preferred embodiment, light from the observation area, defining a first multi-band light signal, enters an opening in the camera. The first multi-band light signal impinges onto the optical filter at an angle selected so that the filter is in tune with the spectral bands characterising the target, that is to say, so that the spectral filtering characteristics of the optical filter are an alignment with the spectral bands of the target (see FIGS. 1, 2, 3A, 3B). The resulting filtered signal is detected and imaged on an appropriate imaging device, such as a detector array, thereby obtaining the "in-band" filtered image.

The filter may be used either in bandpass mode, where the filtered wavelengths are passed on by the filter, or in bandstop mode, where all wavelengths but the filtered ones are passed on by the filter.

If the filter is used in bandpass mode, then only the spectral components, i.e. wavelength bands, of the first multi-band signal which are in alignment with the spectral filtering characteristics of the filter, and therefore in tune with the characteristic spectral bands of the target, are passed on by the filter to the imaging device. The 2D in-band image of the observation area that is obtained shows the observation area with contrasting regions where the target is present. Alternatively, if the filter is used in bandstop mode, then the filter rejects the wavelengths corresponding to the characteristic spectral bands of the target, and the remainder of the first multi-band light signal is passed on by filter. In this case, the in-band image that is obtained shows only the background of the observation area.

c) obtaining an out-of-band filtered image of the observation area using the camera;

Next, using the same camera, an out-of-band image is obtained as depicted in FIGS. 3C and 3D. Preferably, a second multi-band light signal from the observation area impinges onto the optical filter at an angle different from that of the in-band case, so that the filter is slightly out of tune with the spectral profile of the target, that is to say, so that the spectral filtering characteristics of the optical filter are no longer in alignment with the spectral bands of the target (see FIGS. 1, 2, 3C and 3D).

In the bandpass case, the wavelength bands directed by the filter onto the imaging device have the same spectral distribution as the spectral bands characterizing the target, but offset therefrom. The filtered bands are therefore representative of the background of the observation area. Thus, the obtained out-of-band image represents the observation area excluding the target spectral bands. In the bandstop case, the filter will deflect away from the imaging device the wavelengths corresponding to the offset spectral profile of the target, but will let through all other wavelengths, including the wavelengths corresponding to the target and the remaining wavelengths corresponding to the background information. The resulting out-of-band image is therefore representative of the observation area as a whole.

The first and second multi-band light signals required to produce the in-band and out-of-band images respectively may be obtained from two separate multi-band light signals originating from the observation area and received successively at the camera, for example by opening and closing a shutter provided at an opening of the camera. Alternatively, a single multi-band light signal form the observation area received by the camera may be split into the first and second multi-band light signal. In the latter case, the two images can be recorded simultaneously, side-by-side, by the imaging device of the camera (see FIG. 5). The camera may of course include any additional optical element such as mirrors and lenses necessary to redirect and focus light onto any one of the camera components, for example onto the filter or the imaging device, as is well known to those skilled in the art.

d) subtracting one of the in-band filtered image and out-of-band filtered image from the other to obtain the high-contrast image of the observation area.

By subtracting either the in-band filtered image from the out-of-band filtered image or the out-of-band filtered image from the in-band filtered image, a high-contrast image of the observation area highlighting the area where the target is present is obtained, as depicted in FIG. 3E.

If the filter is used in bandpass mode, then the in-band image includes a contribution from the background and a contribution from the target (that may be negative in the case of absorption bands), and the out-of-band image represents the background only. Subtracting the two therefore yields an image emphasising the presence of the target.

If the filter is used in bandstop mode, then the in-band image includes a contribution from the background only, there being an absence of light where the target is present. The out-of-band image includes contributions from both the background and the target. Subtracting the two therefore yields a negative image emphasising the presence of the target.

As will be understood by one skilled in the art, the method above may be used to detect and monitor multiple targets within an observation area, by using different filters each having spectral filtering characteristics matching the spectral profile of one of the targets. A different color may be assigned to the spectral bands of each target under observation to facilitate identification and enhance monitoring of each target. Moreover, the intensity of the assigned color may be modulated so that it represents a relative density of each of the targets present in the observation area. The intensity modulation may indeed be used for the observation of a single target, for example to visually represent the evolution of its density over time.

In this way, real time detection and monitoring of one or more targets in an observation area through successive high contrast images is possible.

Camera According to the Invention

Figure 4:
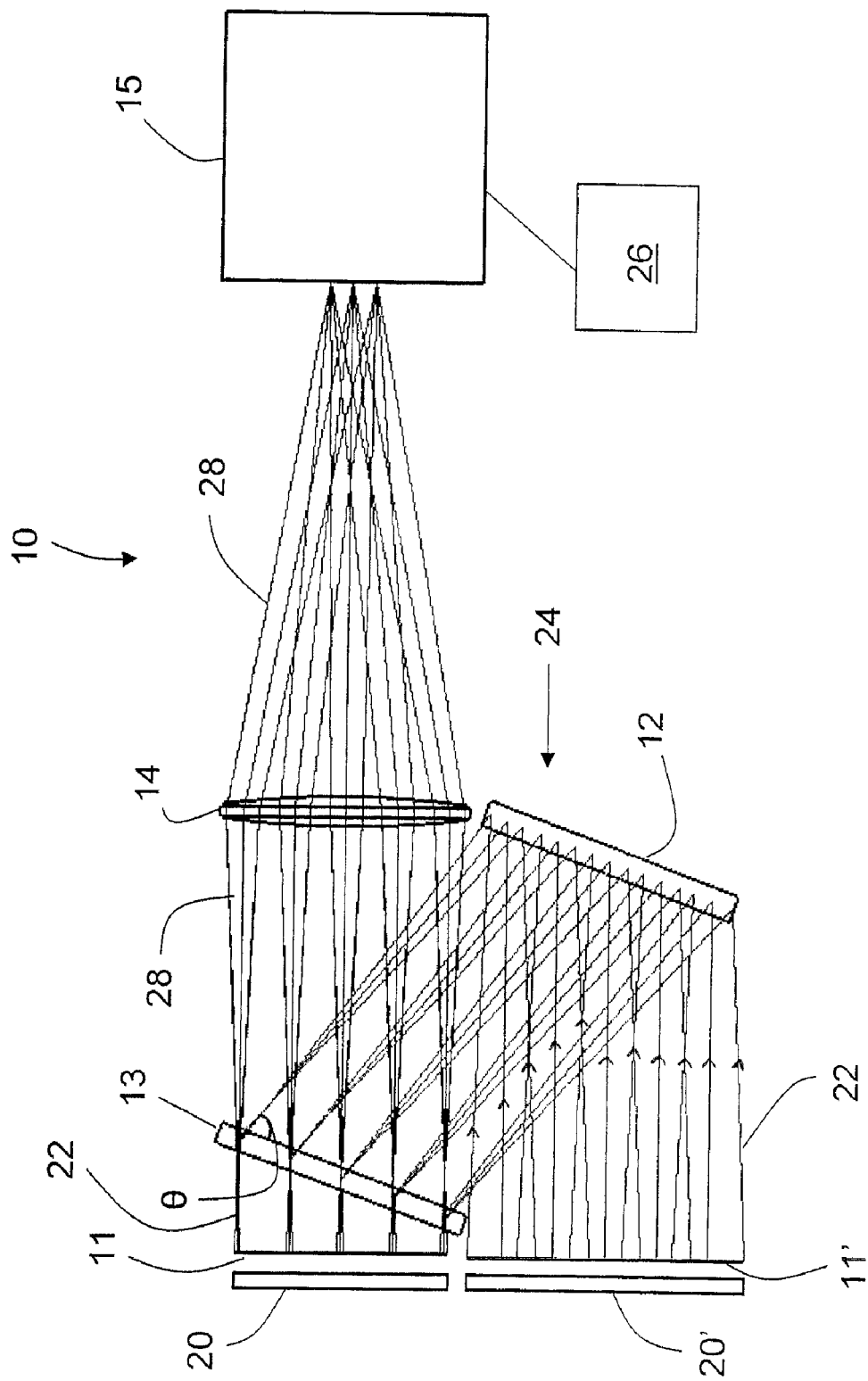
FIG. 4 is a schematic representation of the design of a camera according to one embodiment of the invention.
Figure 5:
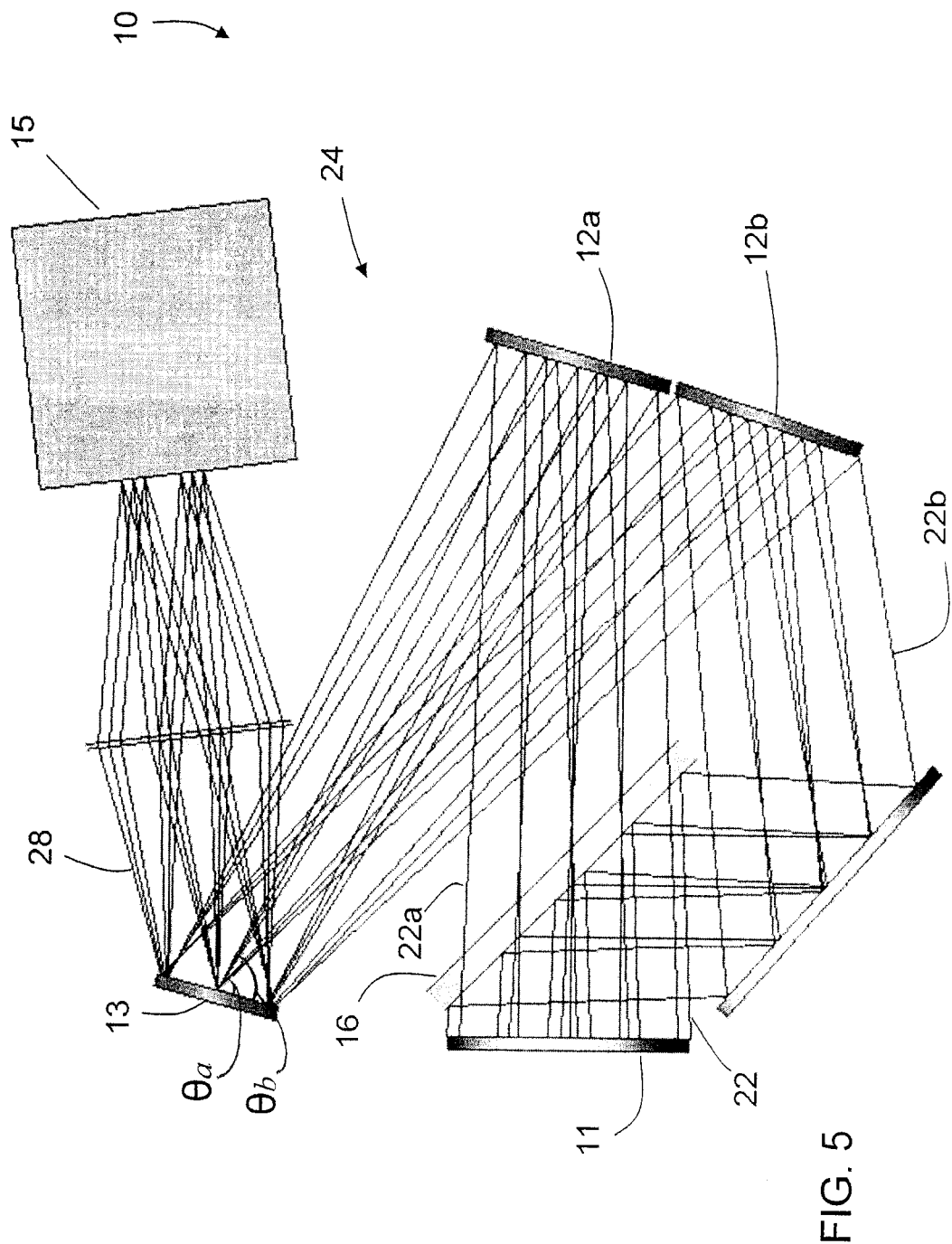
FIG. 5 is a schematic representation of the design of a camera according to another embodiment of the invention.

Referring to FIGS. 4 and 5, and in accordance with another aspect of the present invention, there is provided a camera (10) for obtaining a high-contrast image of an observation area containing one or more targets, each target being characterized by a plurality of predetermined spectral bands.

The camera (10) first includes an optical filter (13) having spectral filtering characteristics matching the spectral bands of the target. The filter therefore selectively separates those wavelengths of an incoming light signal included in these spectral bands from the remainder of the wavelengths present in the light signal.

Preferably, the optical filter (13) is embodied by a Volume Bragg Grating (VBG), also referred to as a Volume Holographic Grating or Volume Phase Hologram. A VBG is a volume grating in which is provided a periodic variation of the index of refraction, allowing the selective deflection of light of a selected wavelength. The variation of the index of refraction may be designed so that the grating filters a plurality of selected wavelengths or wavelength bands. In this manner, a filter having the desired filtering characteristics may be manufactured. The Volume Bragg Grating (VBG) is preferably made of a material such as holographic doped glass, dichromated gelatine or holographic polymers (see US patent application no. 2005/0195484). Volume Bragg Gratings made of holographic doped glass are preferable for narrow band widths (typically less than 0.1% of center wavelength) whereas Volume Bragg Gratings made of dichromated gelatine are preferable for wider band widths.

The filter (13) may be of a reflection type, where the selected wavelengths are reflected by the filter, or a transmission-type, where the selected wavelengths are diffracted by the filter. The orientation of the refractive index modulation with respect to the light input surface will determine the grating type. Reference can be made to Barden et al, "*Volume-Phase Holographic Gratings and the Efficiency of Three Simple Volume-Phase Holographic Gratings*", 2000 PASP, 112:809-820 for examples of both types of gratings.

The match between the filtering characteristics of the filter (13) and the spectral bands characterising the target assumes a predetermined impinging angle of the incoming light onto the input surface of the filter, generally a normal incidence. Changing the impinging angle changes the period of the refractive index perturbations "seen" by the light in the filter, which offsets the wavelengths of the deflected light. This property can be advantageously used for the purposes of the present invention as will be explained below.

In order to observe multiple targets, the filter (13) may include a plurality of sub-filters, each having spectral filtering characteristics matching the spectral bands of one of the targets. The sub-filters may be mounted on a filter wheel, or multiplexed into a single Volume Bragg Grating. One skilled in the art will readily understand that the possibilities for more complex arrangement using the teachings of the present invention are quasi-infinite.

The camera (10) further includes an imaging device (15) for imaging light outputted by the optical filter (13). The imaging device (15) may be embodied by any array of detectors apt to provide a 2D image of a given observation area. It may for example be a CCD photon detector provided with a view screen for detecting the outputted light and displaying an image of the detected light.

An optical arrangement (24) in the camera (10) directs light (22) from the observation area to the optical filter (13). It includes receiving means for receiving light from the observation area. These receiving means may simply be one or more openings (11) in a casing provided for the camera (10), each opening (11) having a shutter for selectively limiting light entering the camera. The optical arrangement (24) has an in-band mode for obtaining an in-band filtered image of the observation area at the imaging device (15), and an out-of-band mode for obtaining an out-of-band filtered image of the observation area at the imaging device (15). It will be understood by one skilled in the art that the optical arrangement (24) may include any number of appropriate optical components. A dispersion compensation system may be used to conserve image quality, as in US patent application no. 2005/0195484.

In the preferred embodiment, in the in-band mode, light (22) from the observation area is selectively made to impinge onto the filter (13) at such an angle as to have the filter (13) in tune with the spectral bands of the target. In other words, the impinging angle is selected so as to provide an alignment of the spectral filtering characteristics of the filter (13) with the spectral bands characterising the target. Thus, only the wavelengths from the spectral profile of the light from the observation area which are in tune, i.e. in alignment, with the filter (13) will be deflected by the filter to the imaging device (15).

In the out-of-band mode, light (22) from the observation area is selectively made to impinge onto the filter (13) at an angle different from that of the in-band case. The impinging angle is such as to provide a non-alignment of the spectral filtering characteristics of the filter (13) with the predetermined band or bands of each target. Thus, the bands from the spectral profile of the light from the target are no longer in tune with the filter (13) and the light deflected to the imaging device (15) is representative of the background of the observation area.

The camera (10) also includes processing means (26) for processing the in-band and out-of band images, which may be embodied by appropriate electronics and accompanying software associated with the imaging device (15). The processing means may be part of the imaging device controls or a separate processor, for example a program algorithm executed by a computer which is in communication with the imaging device. The processing means (26) allow the subtraction of one of the in-band or out-of-band images from the other, thereby obtaining the high contrast image of the target. The processing means (26) may of course perform any other appropriate function. To facilitate the detection and monitoring of the spectral profile of the target, the processing means (26) include colour-coding means for assigning a different colour to the predetermined bands characterising each of the contrast targets as well as modulating means for modulating the different colours in intensity so that the intensity represents the density of each of the targets present in the observation area.

Referring more particularly to FIG. 4, there is shown a first exemplary design of a camera (10) according to one embodiment of the invention. The camera (10) shown has two openings, a top opening (11) and a bottom opening (11'), and a shutter (20, 20') associated with each opening (11, 11') for controlling the entrance of light into the camera (10). The provision of dual openings allows the camera to be used either in bandpass or bandstop mode, as explained below.

Using the bottom opening (11') and corresponding light path, the camera (10) is used in bandpass mode. Multi-band light (22) from the observation area enters, directly or via a collimating system, the bottom opening (11') provided in the camera. The optical arrangement (24) includes in this case a fold mirror (12) redirecting the incoming light (22) onto the optical filter (13). The optical arrangement (24) further includes a pivotable support (not shown) on which the optical filter (13) is mounted so that the impinging angle θ between the light (22) from the mirror (12) and the impinging surface of the filter (13) can be changed. The camera (10) of FIG. 4 acquires the in-band and out-of-band images successively as follows. The optical filter (13) is first oriented so that the impinging angle θ provides for an alignment of the filtering characteristics of the filter (13) with the spectral band characterising the target. Therefore only those wavelength bands of the multi-band light (22) which are in alignment, in tune, with the filter (13) are reflectively deflected by the filter to form a filtered light signal (28) which is directed onto the imaging device (15). In the illustrated example, a focussing lens (14) is provided between the filter (13) and imaging device (15) to focus the filtered light (28) on the latter. The filtered light (28) is detected and imaged by the imaging device (15), producing the in-band image. To obtain the out-of-band image, the filter (13) is tilted slightly so that the impinging angle θ is changed. As a result, the wavelengths reflected towards the imaging device by the filter (13) are out-of-tune with the spectral band characterising the target. The obtained in-band and out-of-band images can then be processed by the processing means to obtain the high-contrast image of the target as explained above.

As will be readily seen by one skilled in the art, the same camera can be used in bandstop mode by using the top opening (11) to receive the incoming light (22). The filter (13) will reflect away the selected in-band and out-of-band wavelengths and pass on to the imaging device (15) the remainder of the received light (22).

Of course, numerous variations on the relative position, the nature and the number of optical components used in the camera can be imagined by one skilled in the art to achieve the same result as in FIG. 4. It will also be understood that a particular camera may be provided with a bandpass mode only or bandstop mode only.

Referring to FIG. 5, there is shown another exemplary design of a camera (10) according to an embodiment of the invention. In this embodiment, the optical arrangement (24) of the camera (10) is fixed—the filter (13) need not be rotated in order to obtain an in-band or out-of-band image. Multi-band light (22) enters the opening (11) and is split using a beam splitter (16)—creating a first light signal (22a) transmitted through the beamsplitter (16) and a second light signal (22b) reflected along a different light path. The first light signal (22a) is reflected using a first fold mirror (12a) onto the filter (13) at an impinging angle $\theta_a$ such that the predetermined spectral bands characterising the spectral profile of the target are in alignment with the spectral characteristics of the filter (13). The filter (13), which is again of a reflection type in the illustrated example, deflects the filtered light towards the imaging device (15) to obtain the in-band image. The second light signal (22b) is also reflected onto the filter (13) using a fold mirror (12b), but at an impinging angle $\theta_b$ slightly different from the impinging angle $\theta_a$ of the first light signal (22a). This difference in angle of impingement translates into the non-alignment of the filter (13) with the predetermined spectral bands characterising the spectral profile of the target and results in an out-of-band image at the imaging device (15). This slight angular difference will also result in a different image location on the imaging device (15), preferably next to the in-band image.

In the two embodiments illustrated in FIGS. 4 and 5, the filter (13) used is of a reflection type. It will of course be understood that a transmission type filter may alternatively be used, with an appropriate positioning of the various components of the camera.

Advantages of the method and camera provided by the present invention include a significantly better detection signal-to-noise ratio by using multiple bands and reduced processing time owing to simultaneous imaging of multiple bands. Moreover, the camera according to the present invention may be used in a wide variety of applications: the detection and monitoring of gaseous emissions in a plant or refinery, changes in the vegetation or high atmospheric gases as observed from space, or glucose and/or other molecules in the blood via retinal imaging.

Although the present invention has been presented herein by way of preferred embodiments thereof, it is to be understood that the invention is not limited to these precise embodiments and that various changes and modifications may be effected therein without departing from the scope or spirit of the present invention.

The invention claimed is:

1. A method for obtaining a high-contrast image of an observation area, said observation area including at least one contrast target, light from said contrast target having a spectral profile characterised by a plurality of predetermined spectral bands, said method comprising the steps of:
   a) providing a camera comprising an optical filter having spectral filtering characteristics matching said plurality of predetermined spectral bands;

b) obtaining an in-band filtered image of said observation area using said camera, said obtaining an in-band filtered image comprising the substeps of:
   i. receiving a first multi-band light signal from said observation area; and
   ii. filtering said first multi-band light signal, said filtering said first multi-band light signal comprising impinging said first multi-band light signal on said filter from an angle selected to provide an alignment of the spectral filtering characteristics of the filter with the plurality of predetermined spectral bands of the contrast target;
c) obtaining an out-of-band filtered image of said observation area using said camera, said obtaining an out-of-band filtered image comprising the substeps of:
   i. receiving a second multi-band light signal from said observation area; and
   ii. filtering said second multi-band light signal, said filtering said second multi-band light signal comprising impinging said second multi-band light signal on said filter from an angle selected to provide a non-alignment of the spectral filtering characteristics of the filter with the plurality of predetermined spectral bands of the contrast target; and
d) subtracting one of said in-band filtered image and out-of-band filtered image from the other to obtain said high-contrast image of the observation area.

2. The method according to claim 1, wherein the substeps b) i. and c) i. of receiving said first and second multi-band light signals, respectively, each comprises opening a shutter provided at an opening of said camera.

3. The method according to claim 1, wherein the substeps b) i. and c) i. of receiving said first and second multi-band light signals, respectively, comprise splitting an incoming multi-band light signal from said observation area into said first and second multi-band light signals.

4. The method according to claim 1, comprising an additional step of assigning a different colour to the plurality of predetermined spectral bands characterising each of said at least one contrast target.

5. The method according to claim 4, comprising an additional step of modulating said different colour in intensity so that said intensity represents a relative density of each of said at least one contrast target.

6. The method according to claim 1, wherein said optical filter is used in bandpass mode to obtain said in-band and out-of-band images.

7. The method according to claim 1, wherein said optical filter is used in bandstop mode to obtain said in-band and out-of-band images.

8. A camera for obtaining a high-contrast image of an observation area, said observation area including at least one contrast target, light from said contrast target having a spectral profile characterised by a plurality of predetermined spectral bands, said camera comprising:
   an optical filter having spectral filtering characteristics matching said plurality of predetermined spectral bands;
   an imaging device for imaging light outputted by said optical filter;
   an optical arrangement for directing light from said observation area onto said optical filter at an impinging angle, said optical arrangement having an in-band mode for obtaining an in-band filtered image of said observation area at said imaging device and an out-of-band mode for obtaining an out-of-band filtered image of said observation area at said imaging device, wherein in said in-band mode said impinging angle is selected to provide an alignment of the spectral filtering characteristics of the filter with the plurality of predetermined spectral bands of the contrast target, and wherein in said out-of-band mode said impinging angle is selected to provide a non-alignment of the spectral filtering characteristics of the filter with the plurality of predetermined spectral bands of the contrast target; and
   processing means for processing said in-band and out-of-band images, said processing comprising subtracting one of said in-band filtered image and out-of-band filtered image from the other to obtain said high-contrast image of the observation area.

9. The camera according to claim 8, wherein said optical filter comprises a Volume Bragg Grating.

10. The camera according to claim 9, wherein the Volume Bragg Grating is made of a material selected from the group consisting of holographic doped glass, dichromated gelatine and holographic polymers.

11. The camera according to claim 8, wherein said optical filter comprises a plurality of sub-filters, each of said sub-filters matching the spectral profile of one of said at least one contrast target.

12. The camera according to claim 11, wherein said processing means comprise color coding means for assigning a different colour to the plurality of predetermined spectral bands characterising each of said at least one contrast target.

13. The camera according to claim 12, wherein said processing means comprise modulating means for modulating said different colour in intensity so that said intensity represents a relative density of each of said at least one contrast target.

14. The camera according to claim 8, wherein said optical arrangement comprises receiving means for receiving said light from the observation area.

15. The camera according to claim 14, wherein said receiving means comprises at least one aperture.

16. The camera according to claim 15, wherein said receiving means comprise a shutter selectively providing access to said at least one aperture.

17. The camera according to claim 8, wherein said optical arrangement comprises a support for mounting said filter, said support being pivotable to change said impinging angle.

18. The camera according to claim 8, wherein said optical arrangement comprises a light splitter for splitting said light from the observation area into a first and a second multi-band light signal, said first and second multi-band light signals being respectively directed to said optical filter at the impinging angles of the in-band and out-of-band modes.

19. The camera according to claim 8, wherein said imaging device receives light reflected by said optical filter.

20. The camera according to claim 8, wherein said imaging device receives light transmitted by said optical filter.

21. The camera according to claim 8, wherein said optical filter is in bandpass mode to obtain said in-band and out-of-band images.

22. The camera according to claim 8, wherein said optical filter is in bandstop mode to obtain said in-band and out-of-band images.

* * * * *